United States Patent [19]

Adair

[11] 4,142,516

[45] Mar. 6, 1979

[54] URETHRAL CONTRACEPTION DEVICE AND METHOD OF APPLYING SAME

[76] Inventor: Edwin L. Adair, 7850 Platte Canyon Rd., Littleton, Colo. 80120

[21] Appl. No.: 685,281

[22] Filed: May 11, 1976

[51] Int. Cl.² ............... A61B 19/00; A61M 29/00
[52] U.S. Cl. ................................. 128/1 R; 128/341
[58] Field of Search .................. 128/1, 341, 345, 343, 128/348

[56] References Cited

U.S. PATENT DOCUMENTS

| 1,039,061 | 9/1912 | Jentzsch | 128/343 |
| 2,085,368 | 6/1937 | Kendall | 128/341 |
| 3,042,021 | 7/1962 | Read | 128/348 X |

Primary Examiner—Stephen C. Pellegrino
Attorney, Agent, or Firm—Sheridan, Ross, Fields & McIntosh

[57] ABSTRACT

Birth control apparatus and method characterized by a ring, adapted to be inserted through the male urethra, and placed in the bladder neck sphincter to maintain same open. During ejaculation, seminal fluid is discharged into the bladder and voided therefrom at a later time. In a preferred form, the ring is contracted to sufficiently small size to permit it to be inserted through the urethra and, after being placed in the sphincter, expanded to larger size, locking same against unauthorized movement therefrom.

6 Claims, 5 Drawing Figures

URETHRAL CONTRACEPTION DEVICE AND METHOD OF APPLYING SAME

BACKGROUND OF THE INVENTION

As is well known, conception by the female may be prevented by the male, while retaining normal ejaculation into the vagina, in several ways which include the use of a condom or by a vasectomy operation which prevents passage of fertile sperm from the testicles to the seminal sac. Withdrawal, just prior to ejaculation, has also been practiced. It is also known that patients who have experienced surgical removal of the bladder neck and its sphincter are incapable of effecting conception since the seminal fluid is discharged into the bladder, rather than outwardly through the urethra. Such type of operation, however, is major and is peformed only for removal of diseased tissue, rather than for preventing conception. Even if such operation were performed solely for preventing conception, it would not be available to most of the world's population. Moreover, it is questionable whether it would ever be performed for its incidental result of contraception. It is apparent, however, that if the incidental result could be obtained without surgical removal of the bladder neck and possible post-operative complications connected therewith, an effective means for contraception could be attained. Also, if such means could be optionally used, contraception or non-contraception would be possible as distinguished from the irreversible effects of a vasectomy. To be practical, moreover, it should be inexpensive, require no surgery, and be applicable or removable by any competent urologist at a minimal cost. It is further apparent that such means would be of great advantage, particularly in overpopulated countries, such as in parts of the Orient, where little population control exists.

SUMMARY OF THE INVENTION

The present invention provides the means just referred to in the form of a device which may be inserted through the urethra and disposed within the iris or sphincter at the bladder neck to retain it open at all times which permits ejaculation of semen into the bladder. After intercourse the semen may be voided through the urethra along with any urine which may be present in the bladder. In a preferred embodiment, the device may be a C-shaped strip of material which may be rolled into a tight spiral small enough to pass through the urethra to the bladder neck. It is then released and, due to its resilience or memory it expands to form an open tube which retains the bladder neck sphincter open to permit seminal fluid to be discharged therethrough and into the bladder.

In accordance with the foregoing, one of the objects of the invention is the provision of a birth control device which may be inserted in or removed from a bladder sphincter through the urethra and without surgery.

Another object is the provision of a device, contractable to a size to pass through a urethra and thence expandable within a bladder sphincter to retain same therein.

Further objects are to retain normal sensations of coitus, not present with the use of a condom, and to render conception reversible, not present after a vasectomy, or at least not invariably reversible as presently known.

Still further objects, advantages, and salient features will become more apparent from the detailed description to follow, the appended claims, and the accompanying drawing, to now be briefly described.

DETAILED DESCRIPTION OF THE INVENTION

Figure 1:
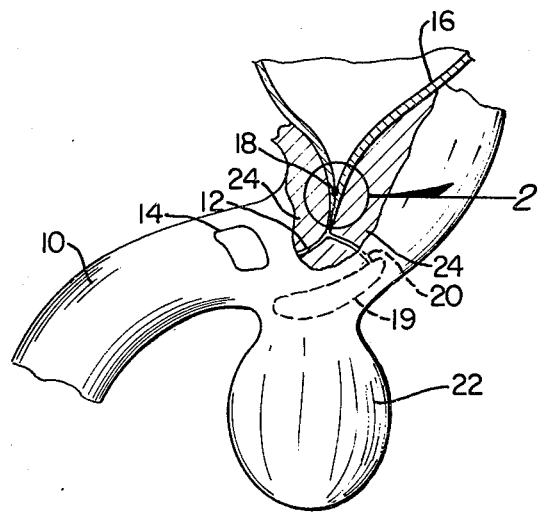
FIG. 1 generally depicts the reproduction system of a human male.

Referring now to the drawing, and first to FIG. 1, as is well known, a male reproduction system comprises a penis 10, including a urethra 12 and external sphincter 14, the proximal end (relative to the bladder) of the urethra communicating with a bladder 16 through a bladder sphincter 18. Seminal fluid flows from a seminal supply sac 19 to the urethra, during ejaculation, at a point downstream from the bladder sphincter and through a seminal sac valve 20. In the normal male, sperm is supplied to the seminal sac from testes 22. Of lesser importance for an understanding of the invention, prostate 24 is disposed adjacent the bladder sphincter and proximal end (relative to the patient's body) of the penis. During ejaculation of the normal male, the bladder sphincter is closed, preventing flow of seminal seminal fluid to the bladder, the fluid thus flowing through the urethra to the distal end of the penis, which is actually a by-pass flow, since the normal tendency of the flow of the seminal fluid is toward the bladder. Thus, if the bladder sphincter remains open during ejaculation, flow of the seminal fluid will be bypassed toward and into the bladder. The subject invention attains this end.

Figure 2:
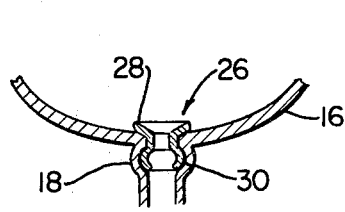
FIG. 2 is an enlargement of Detail 2, FIG. 1.

As best shown in FIG. 2, the subject invention comprises a ring 26 disposed within bladder sphincter 18, retaining same open and permitting flow of the fluid therethrough and into bladder 16, rather than to the distal end of the urethra and penis.

Figure 4:
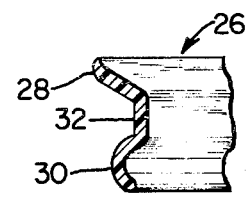
FIG. 4 is an enlarged section taken on line 4-4, FIG. 3.
Figure 3:
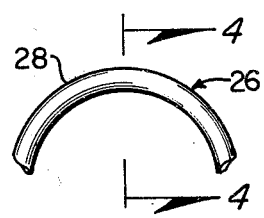
FIG. 3 is a top plan of a preferred form of the invention in its relaxed condition, prior to insertion thereof through a urethra.

Ring 26, in its relaxed state, before being placed within the bladder sphincter, as shown in FIGS. 3 and 4, comprises a strip of material having a flange 28 at one end and a bulge 30 adjacent its other end, forming annular groove 32 therebetween which seats within the bladder sphincter, the flange being within the bladder adjacent the sphincter. As will be apparent, the flange properly locates the device within the sphincter and locks it against outward movement therethrough and the bulge and groove locks same against inward movement therethrough.

Figure 5:
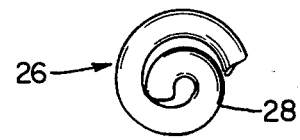
FIG. 5 is a top plan, like FIG. 3, illustrating the invention in coiled form, prior to installation within a bladder sphincter.

To insert the device through the urethra, it is first contracted into a tight coil, as illustrated in FIG. 5, and placed within a suitable instrument, such as a cystoscope. The cystoscope is then inserted into the urethra to proper position and, with a suitable instrument, the device is released within the bladder sphincter. Due to its resilience or memory, the device tends to return to its normal relaxed state, thus becoming a split tube resiliently urged against the bladder sphincter. If, at some time, it is desired to effect conception, the device may be removed in like manner.

Examplary materials for the ring include high density polyethylene, polypropylene, Teflon and silicone rubber which may be injection moulded to the shape shown in FIG. 3. These materials, as distinguished from normal resilient materials (such as metals) which strictly obey Hooke's law, may be distorted far beyond the normal limits of elasticity, yet, due to their "memory," tend to return to their unstressed shapes. In a stress-strain curve, they may thus be strained and distorted beyond the limit of elasticity of truly resilient materials and gradually return along the curve rather than along the hysterisis loop of permanent deformation.

While an exemplary form of the invention has been disclosed as an expandable ring-like device, it is to be understood that functionally equivalent devices will become apparent to those skilled in the art, which are contemplated within the purview of the invention, except as limited by the appended claims.

What is claimed is:

1. Apparatus for preventing the normal ejaculation of semen from a human male urethra into a vagina of a human female during coitus, said apparatus comprising:
    an arcuate, deformable ring-like member positionable within a male bladder sphincter which is normally closed to the urethra during ejaculation for retaining the sphincter open so that semen may by-pass to the bladder during ejaculation from which it may later be voided, said member being deformable prior to being installed to a sufficiently small size to be inserted in the bladder sphincter, the member then being expandable due to its memory and tending to return toward its original shape, the shape after expansion being a substantially closed ring of a size limited by the bladder sphincter, said member including;
    first means positionable within the bladder adjacent the bladder sphincter for preventing outward movement therefrom into the urethra, and
    second means spaced from said first means and engageable within and by the bladder sphincter for preventing inward movement thereof into the bladder so that said device will remain locked within the bladder sphincter against movement therefrom.

2. Apparatus in accordance with claim 1 wherein said first means comprises a surrounding flange of a size larger than the bladder sphincter opening to prevent outward movement therethrough, and said second means comprising an annular abutment which would tend to enlarge the bladder sphincter opening if moved axially relative thereto, the bladder sphincter being of minimum size between said first and second means.

3. Apparatus in accordance with claim 1 wherein said member, prior to being released in the bladder sphincter, is sufficiently small to be passed through the urethra by an instrument, such as a cystoscope, thereby obviating surgery to install same within the bladder sphincter.

4. Apparatus, in accordance with claim 1, wherein said member is in the form of a coil.

5. A method of installing a contraceptive for preventing the normal ejaculation of semen from a human male urethra to a vagina of a human female during coitus, said contraceptive including a resilient, ring-like member for placement within a male bladder sphincter, the member normally being larger than the bladder sphincter, said method comprising the steps of:
    reducing the member to a size to be disposed within the bladder sphincter prior to insertion thereof;
    passing the member in reduced size through the urethra;
    placing the member within the bladder sphincter; and
    expanding the member due to its resilience within the bladder sphincter to retain the bladder sphincter in open condition to by-pass semen to the bladder during ejaculation so that the semen will be harmlessly discharged with the contents of the bladder the next time the bladder is voided.

6. A method in accordance with claim 5 wherein said member is in the form of a coil and said reducing step includes coiling the member to a size to be disposed in a bladder sphincter and said expanding stage includes uncoiling the member within the bladder sphincter.

* * * * *